(12) United States Patent
Francke

(10) Patent No.: US 7,164,748 B2
(45) Date of Patent: Jan. 16, 2007

(54) ARRANGEMENT AND METHOD FOR OBTAINING IMAGING DATA

(75) Inventor: Tom Francke, Sollentuna (SE)

(73) Assignee: Xcounter AB, Danderyd (SE)

( * ) Notice: Subject to any disclaimer, the term of this patent is extended or adjusted under 35 U.S.C. 154(b) by 6 days.

(21) Appl. No.: 10/917,531

(22) Filed: Aug. 13, 2004

(65) Prior Publication Data

US 2005/0226368 A1    Oct. 13, 2005

Related U.S. Application Data

(63) Continuation-in-part of application No. 10/849,209, filed on May 20, 2004.

(30) Foreign Application Priority Data

Mar. 30, 2004    (SE) .................................... 0400822

(51) Int. Cl.
*G01N 23/083* (2006.01)
(52) U.S. Cl. .......................... 378/22; 378/25; 378/196; 378/197
(58) Field of Classification Search .................... 378/9, 378/21, 22, 23, 24, 25, 26, 27, 19, 130, 13, 378/196, 197; 250/363, 363.02, 382, 389, 250/363.05, 454.11
See application file for complete search history.

(56) References Cited

U.S. PATENT DOCUMENTS 4,084,094 A    4/1978   Froggatt
4,101,774 A    7/1978   Elzinga et al.
4,349,740 A    9/1982   Grassmann et al.
4,357,708 A   11/1982   Baeker
4,566,112 A    1/1986   Linde et al.
4,665,540 A    5/1987   Kunert
4,707,608 A   11/1987   DiBianca ................... 250/389

(Continued)

FOREIGN PATENT DOCUMENTS

CA    2277251 A1    1/2001

(Continued)

OTHER PUBLICATIONS

Search Report.

(Continued)

*Primary Examiner*—Edward J. Glick
*Assistant Examiner*—Anastasia S. Midkiff
(74) *Attorney, Agent, or Firm*—Harness, Dickey & Pierce

(57) ABSTRACT

A scanning-based arrangement for obtaining imaging data of an object at high repetition rate comprises a support structure; scanning-based apparatuses fixedly arranged on the support structure and each including (i) a radiation source, and (ii) a radiation detector comprising a stack of line detectors, each being directed towards the radiation source to allow a ray bundle of radiation to enter the line detector; an object table arranged in the radiation path of one of the scanning-based apparatuses; and a device provided for rotating the support structure relative the object table so that the object table will successively be arranged in the radiation path of each of the scanning-based apparatuses, during which rotation each of the line detectors in each of the radiation detectors is adapted to record a plurality of line images of radiation as transmitted through the object.

57 Claims, 4 Drawing Sheets

U.S. PATENT DOCUMENTS

| | | | |
|---|---|---|---|
| 4,780,897 A | 10/1988 | McDaniel et al. ............ 378/62 |
| 4,800,580 A | 1/1989 | Houtman et al. ............. 378/71 |
| 5,008,907 A | 4/1991 | Norman et al. .............. 378/65 |
| 5,025,376 A | 6/1991 | Bova et al. |
| 5,060,246 A | 10/1991 | Van Der Brug et al. |
| 5,331,553 A | 7/1994 | Muehllehner et al. |
| 5,518,578 A | 5/1996 | Persells et al. |
| 6,067,342 A | 5/2000 | Gordon |
| 6,118,125 A | 9/2000 | Carlson et al. |
| 6,236,709 B1 | 5/2001 | Perry et al. |
| 6,242,743 B1 | 6/2001 | DeVito et al. |
| 6,303,935 B1 | 10/2001 | Engdahl et al. |
| 6,320,929 B1 | 11/2001 | Von Der Haar |
| 6,337,482 B1 | 1/2002 | Francke |
| 6,353,227 B1 | 3/2002 | Boxen ..................... 250/363.1 |
| 6,365,902 B1 | 4/2002 | Francke et al. |
| 6,373,065 B1 | 4/2002 | Francke et al. |
| 6,381,487 B1* | 4/2002 | Flohr et al. ................. 600/425 |
| 6,385,282 B1 | 5/2002 | Francke et al. |
| 6,414,317 B1 | 7/2002 | Francke et al. |
| 6,476,397 B1 | 11/2002 | Francke |
| 6,477,223 B1 | 11/2002 | Francke |
| 6,501,822 B1 | 12/2002 | Roder |
| 6,522,722 B1 | 2/2003 | Francke |
| 6,546,070 B1 | 4/2003 | Francke |
| 6,570,954 B1 | 5/2003 | Rasche et al. |
| 6,600,804 B1 | 7/2003 | Francke et al. |
| 6,731,065 B1 | 5/2004 | Francke et al. |
| 6,760,399 B1 | 7/2004 | Malamud |
| 6,784,436 B1 | 8/2004 | Francke |
| 6,794,656 B1 | 9/2004 | Francke et al. |
| 6,823,044 B1* | 11/2004 | Rosner ..................... 378/98.8 |
| 6,970,531 B1 | 11/2005 | Eberhard et al. |
| 2002/0003860 A1 | 1/2002 | Francke et al. ............ 378/98.8 |
| 2003/0048935 A1* | 3/2003 | Keren ........................ 382/130 |
| 2003/0155519 A1 | 8/2003 | Francke et al. |
| 2004/0264634 A1* | 12/2004 | Claus et al. .................. 378/21 |

FOREIGN PATENT DOCUMENTS

| | | |
|---|---|---|
| DE | 3035529 A1 | 5/1982 |
| EP | 0244292 A1 | 11/1987 |
| GB | 2061055 | 5/1981 |
| WO | WO 00/62094 | 10/2000 |

OTHER PUBLICATIONS

International Search Report dated Jun. 15, 2005 for International application No. PCT/SE 2005/000386.

International-Type Search Report dated Oct. 29, 2004 for International-type search request No. SE 04/00182.

* cited by examiner

ARRANGEMENT AND METHOD FOR OBTAINING IMAGING DATA

CROSS-REFERENCE TO RELATED APPLICATIONS

This application claims priority of Application No. 0400822-3 filed in Sweden on Mar. 30, 2004 under 35 U.S.C. § 119 and is a continuation-in-part of co-pending application Ser. No. 10/849,209, filed in the U.S. on May 20, 2004, under 35 U.S.C. § 120; the entire contents of both of which are hereby incorporated by reference in their entirety.

FIELD OF THE INVENTION

The invention relates generally to scanning-based arrangements and methods for obtaining imaging data at high repetition rates for time-resolved examination of an object.

BACKGROUND OF THE INVENTION AND RELATED ART

An X-ray medical diagnostic method such as mammography is a low-dose procedure that creates one or more images of a part of a patient such as a breast thereof, which is to be examined, e.g. for detection of early stages of cancer.

The mammography diagnostic procedure generally includes obtaining two images of each of the patient's breasts, one from above and one from the side. A physician or radiologist then reviews the images of the breast, i.e., mammograms, to identify any breast cancer.

While this procedure is one of the best methods of detecting early forms of breast cancer, it is still possible for the detection of breast cancer to be missed by a physician or radiologist reviewing the mammograms. For example, breast cancer may be missed by being obscured by radiographically dense, fibroglandular breast tissue.

Tomosynthesis imaging, in which a plurality of images is acquired at different angles, has been studied in an effort to detect early forms of breast cancer. By combining the plurality of images, it is possible to reconstruct any plane in the breast being imaged that is parallel to the detector. The higher number of images is utilized, the better image quality in the reconstructed tomosynthesis images is obtained.

Angiography is a radiological method for examination of blood or lymph vessels. A catheter is inserted into the vessel e.g. by Seldinger technique and a water soluble contrast agent is injected into the vessel, after which a series of X-ray images of the vessel is taken. Examinations of arteries, veins and lymph vessels are denoted arteriography, flebography, and lymphography, respectively. Arteriography, being a commonly applied examination method, includes angiocardiography for examination of the heart, coronary angiography for examination of the coronary arteries of the heart, and aortography for examination of the aorta.

Fluoroscopy is a technology for visualizing ionizing radiation. A glass plate with a surface layer of fluorescing material, e.g. $BaPt(CN)_4$ emits visible light when being exposed to gamma rays. Fluoroscopy is used for visualizing or frequency converting images, e.g. of high repetition rate, as taken by a high speed X-ray camera, for examination of the heart of a patient for instance.

Various line detectors for detecting ionizing radiation are known in the art. While such detectors provide for instantaneous one-dimensional imaging, two-dimensional imaging can only be performed by means of scanning the line detector, and optionally the radiation source, in a direction traverse to the one-dimensional detector array. To use such a detector in e.g. tomosynthesis, wherein a plurality of images has to be acquired at different angles would be very time consuming. For e.g. angiography, wherein time-dependent variations are observed, the situation is even worse.

A scanning-based radiation detector arrangement for two-dimensional imaging of an object is disclosed in the US patent publication No. 2003/0155519 A1. The arrangement comprises a plurality of one-dimensional detector units, each comprising an entrance slit, through which ionizing radiation as transmitted through the object is entered, and being arranged for one-dimensional imaging of the ionizing radiation, wherein the detector units are arranged in an array on a support with their respective entrance slits being parallel with each other and facing the source of the ionizing radiation. The detector arrangement further includes a rotating device for rotating the detector unit array in a plane perpendicular to the direction of the ionizing radiation, while the detector units are arranged to repeatedly detect, hence creating a series of two-dimensional images of the object.

SUMMARY OF THE INVENTION

The prior art scanning-based radiation detector arrangement described above is not suitable to be used for obtaining tomosynthesis data since the one-dimensional detector units are not arranged so that they are capable of providing two-dimensional images of the object at different angles.

Further, the algorithms needed for reconstruction of two-dimensional images may be slow and complex depending on the positions of the one-dimensional detector units relative each other and relative the axis of rotation.

Still further, there is very little space close to the axis of rotation, which limits the number of one-dimensional detector units, and thus the spatial resolution obtainable, there. Some of the embodiments are not at all capable of measuring at the axis of rotation.

Yet further, and maybe of outermost importance, the prior art arrangement uses only one radiation source, and this limits severely the maximum repetition rate of the recording of the two-dimensional images of the object and/or the spatial resolution obtained in the two-dimensional images. During the measurement, the radiation source can not be switched off and cooled, and therefore the maximum output radiation flux of the radiation source limits the speed by which the measurement can be performed.

A main aim of the invention is therefore to provide a scanning-based arrangement and a method, respectively, for obtaining imaging data of an object at higher speed than what is obtainable by using scanning-based apparatuses and methods of the prior art.

In this respect there is a particular aim to provide such an arrangement and such a method, which are capable of collecting, by means of scanning-based detection, imaging data in order to reconstruct three-dimensional images of the object at high repetition rate.

A further aim of the invention is to provide such an arrangement and such a method, which is operable, while exposing the object for a low radiation dose.

A still further aim of the invention is to provide such an arrangement and such a method, which are uncomplicated and can produce high-quality two- and three-dimensional images of the object with high spatial resolution, high sensitivity, high signal-to-noise ratio, high dynamic range, high image contrast, and low noise from overlaying tissue.

A yet further aim of the invention is to provide such an arrangement and such a method, which are reliable, accurate, and inexpensive.

A still further aim of the invention is to provide such an arrangement and such a method, by which tomosynthesis data is obtainable.

A yet further aim of the invention is to provide such an arrangement and such a method, which do not need the use of a complete computerized tomography (CT) apparatus to obtain two- or three-dimensional images with high spatial resolution.

Still further aims of the invention are to provide such an arrangement and such a method, which can be used in angiography and fluoroscopy.

A yet further aim of the invention is to provide such an arrangement and such a method, which provides for the employment of fast and simple image reconstruction algorithms.

These objects, among others, are attained by arrangements and methods as claimed in the appended claims.

According to one aspect of the present invention a scanning-based arrangement for obtaining imaging data of an object at high repetition rate is provided, the arrangement comprising a support structure, and scanning-based apparatuses fixedly arranged on the support structure and each including (i) a radiation source, and a radiation detector comprising a stack of line detectors, each being directed towards the radiation source to allow a ray bundle of radiation to enter the line detector. The arrangement comprises further an object table arranged in the radiation path of one of the scanning-based apparatuses; and a device provided for rotating the support structure relative the object table so that the object table will successively be arranged in the radiation path of each of the scanning-based apparatuses. During the rotation, each of the line detectors in each of the radiation detectors is adapted to record a plurality of line images of radiation as transmitted through the object.

The data from the apparatus is excellent to be used in tomosynthesis or laminographic imaging, and in angiography, as well as in fluoroscopy The line detectors uses are preferably, but not exclusively, gaseous-based parallel plate detectors. Other line detectors that may be used include scintillator-based arrays, CCD arrays, TFT- and CMOS-based detectors, liquid detectors, and diode arrays, e.g. PIN-diode arrays with edge-on, near edge-on or perpendicular incidence of X-rays.

Further characteristics of the invention and advantages thereof, will be evident from the detailed description of preferred embodiments of the present invention given hereinafter and the accompanying FIGS. 1–4, which are given by way of illustration only, and thus, are not limitative of the present invention.

DESCRIPTION OF PREFERRED EMBODIMENTS

Figure 1:
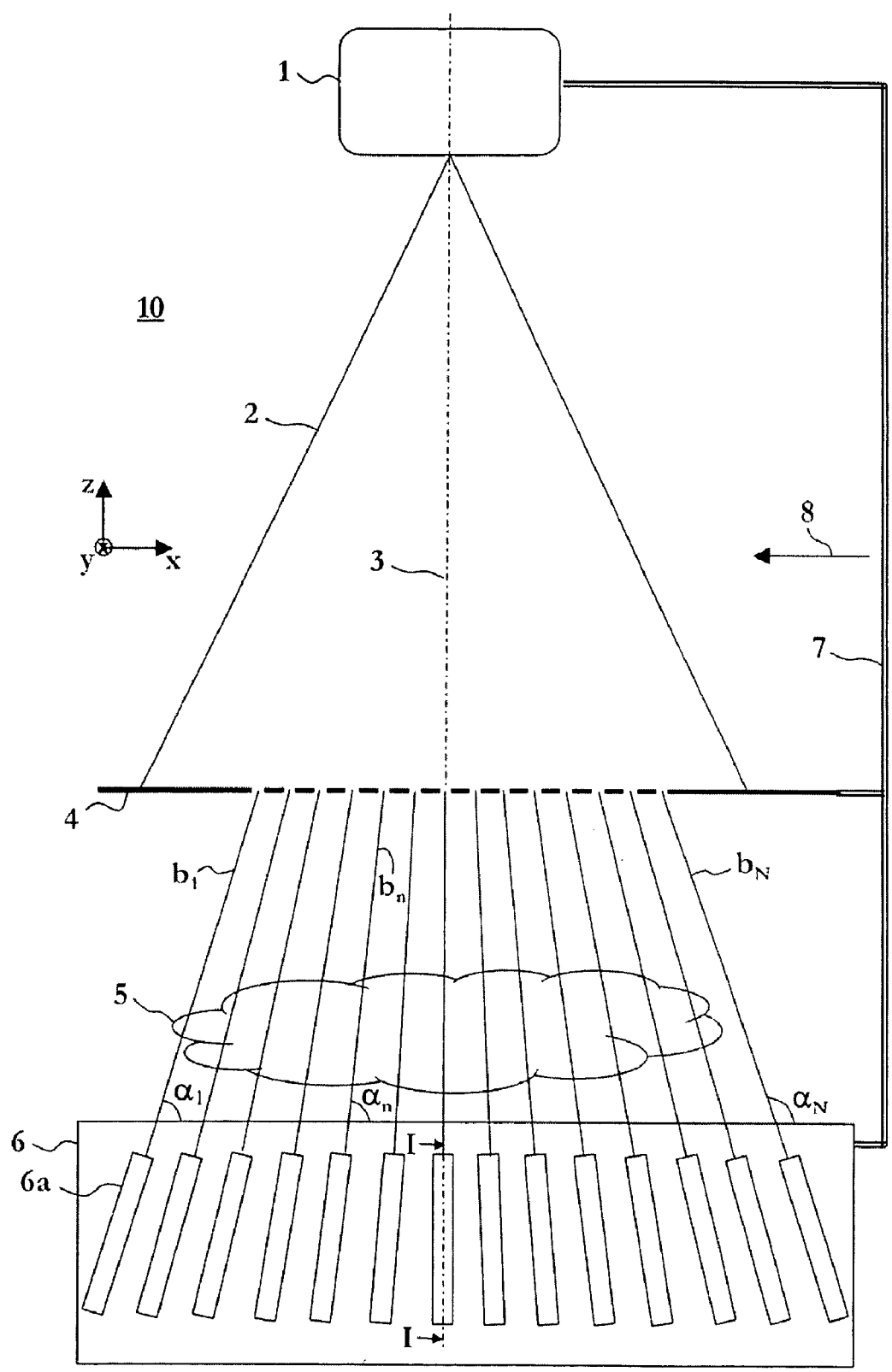
FIG. 1 illustrates schematically, in a side view, an apparatus for obtaining tomosynthesis or other imaging data for x-ray examination of an object.

An apparatus 10 for obtaining tomosynthesis or other imaging data for x-ray examination of an object 5 is shown in FIG. 1. The apparatus 10 comprises an X-ray source 1, which produces X-rays 2 centered around an axis of symmetry 3, which axis is parallel with the z axis, a collimator 4, a radiation detector 6, and a structure 7 for rigidly connecting the X-ray source 1, the collimator 4, and the radiation detector 6 to each other.

The radiation detector 6 comprises a stack of line detectors 6a, each being directed towards the divergent radiation source 1 to allow a respective ray bundle $b_1, \ldots, b_n, \ldots, b_N$ of the radiation 2 that propagates in a respective one of a plurality of different angles $\alpha_1, \ldots, \alpha_n, \ldots, \alpha_N$ with respect to the front surface of the radiation detector 6 to enter the respective line detector 6a.

The collimator 4 may be a thin foil of e.g. tungsten with narrow radiation transparent slits cut or etched away, the number of which corresponds to the number of line detectors 6a of the radiation detector 6. The slits are aligned with the line detectors 6a so that X-rays passing through the slits of the collimator 4 will reach the detector units 6a, i.e. as the respective ray bundles $b_1, \ldots, b_n, \ldots, b_N$. The collimator 4, which is optional, prevents radiation, which is not directed directly towards the line detectors 6a, from impinging on the object 5 to be examined, thereby reducing the radiation dose to the object. This is advantageous in all applications where the object is a human or an animal, or parts thereof.

In U.S. patent application Ser. No. 10/657,241 is disclosed to use such a detector apparatus for linear scanning of the object 5 to obtain tomosynthesis data thereof in order to reconstruct two-dimensional and even three-dimensional images of the object 5. The contents of the above U.S. Patent Application are hereby incorporated by reference.

During such scanning the device 7 moves the radiation source 1, the collimator 4, and the radiation detector 6 relative the object 5 in a linear manner parallel with the front of the radiation detector as being indicated by arrow 8, while each of the line detectors 6a records a plurality of line images of radiation as transmitted through the object 5 in a respective one of the different angles $\alpha_1, \ldots, \alpha_n, \ldots, \alpha_N$. The scanning of the object 5 is preferably performed a length, which is sufficiently large so that each one of the line detectors 6a can be scanned across the entire object of interest to obtain, for each of the line detectors 6a, a two-dimensional image of radiation as transmitted through the object 5 in a respective one of the different angles $\alpha_1, \ldots, \alpha_n, \ldots, \alpha_N$.

Figure 2A:
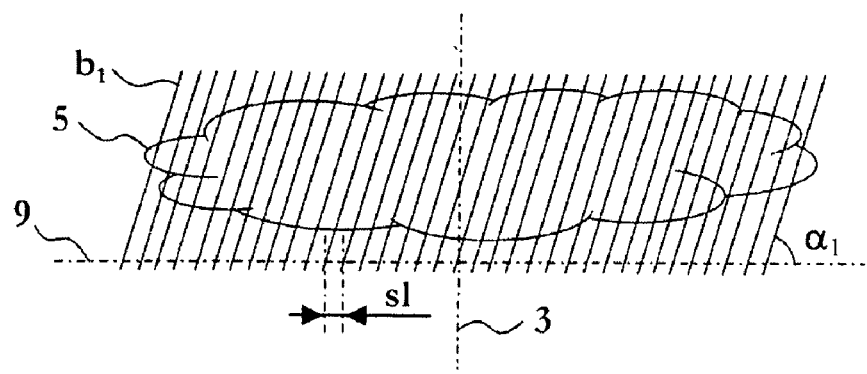
FIGS. 2a–c illustrate each schematically, in a side view, a particular X-ray bundle as it traverses the examination object during scanning by the apparatus of FIG. 1.
Figure 2B:
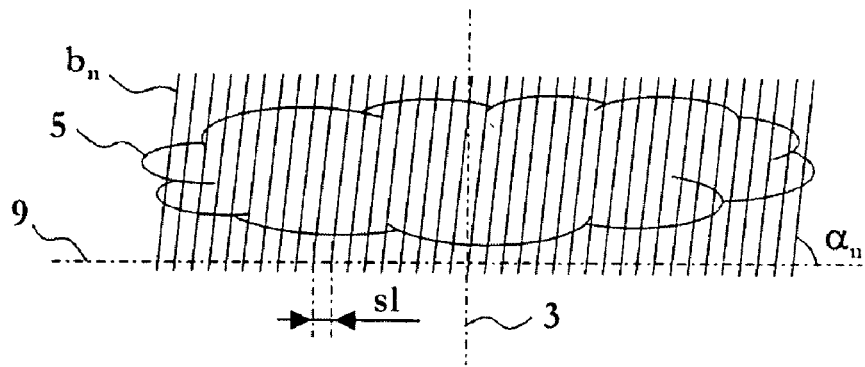
Figure 2C:
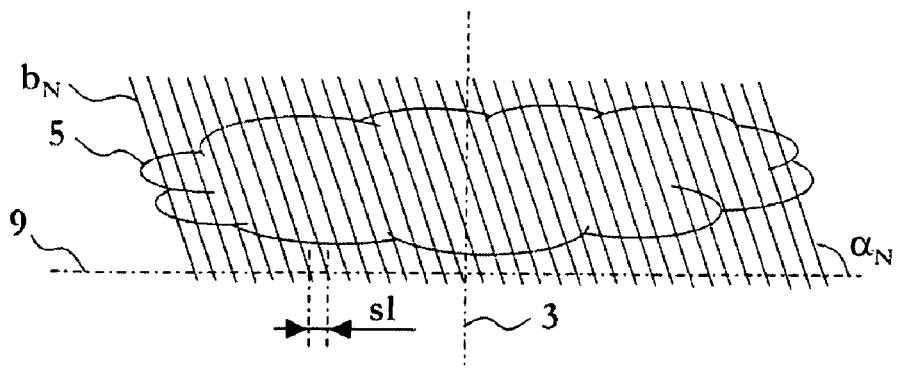

In FIGS. 2a–c three different X-ray bundles b1, bn, and bN are schematically illustrated as they traverse the examination object 5 during scanning by the apparatus of FIG. 1. Reference numeral 9 indicates a plane parallel with the x axis, which coincides with the scanning direction 8 and with the front of the radiation detector 2.

As can be seen in FIGS. 2a–c each line detector/X-ray bundle pair produces a complete two-dimensional image at a distinct one of the different angles. FIG. 2a illustrates the formation of a two-dimensional image of radiation transmitted through the object at an angle $\alpha_1$, FIG. 2b illustrates the formation of a two-dimensional image of radiation transmitted through the same object, but at an angle $\alpha_n$, and FIG. 2c illustrates the formation of a similar two-dimensional image, but at an angle $\alpha_N$.

While such a detector scanning technique provides for the recording of tomosynthesis data of the object, i.e. the simultaneous recording of a number of two-dimensional X-ray transmission images at high speed, it is not suitable to record several images one after each other to observe time dependent examination, such as e.g. positioning of catheters, and to visualize matter in motion, such as e.g. heart, blood, contrast agents, etc., since the scanning movement has to be retarded, stopped, and accelerated in the opposite direction in order to perform a second scan of the object. Such actions are time-consuming and suffer from stability and alignment problems due to the strong forces the detectors experience during the retardations and accelerations.

Further, to obtain a large angular spread of the tomosynthesis data, i.e. a large opening angle of the radiation irradiating the detector apparatus, the detector apparatus has to be long in the scanning direction, which gives a long scanning distance. The scanning speed has therefore to be high, which puts higher demands on the retardation and acceleration of the detector apparatus at the start and end of the scanning movement.

In computerized tomography (CT) there is a trend today to record more and more images per second by increasing the rotational speed, and to use more and more detector rows, e.g. 4, 8 and even 16 rows, in a CT line detector to obtain time-resolved measurements. Lately, discussions to use 64 and up to 256 rows of detectors have been made. The costs for the detector increase to unreasonable high levels for detectors having such many detector rows.

When the number of images per second increases the radiation dose to the patient, which is high enough already, will increase further. One goal of CT today is to be capable of recording time-resolved three-dimensional images of e.g. a heart.

In angiography time-dependent processes of blood or lymph vessels are examined, which puts requirements on the repetition rate of the detector used.

In order to be capable of performing time-resolved tomosynthesis, or other imaging measurements such as e.g. angiographic imaging measurements, with high repetition rate using the scanning-based technique described above several changes and modifications have to be made.

Figure 3:
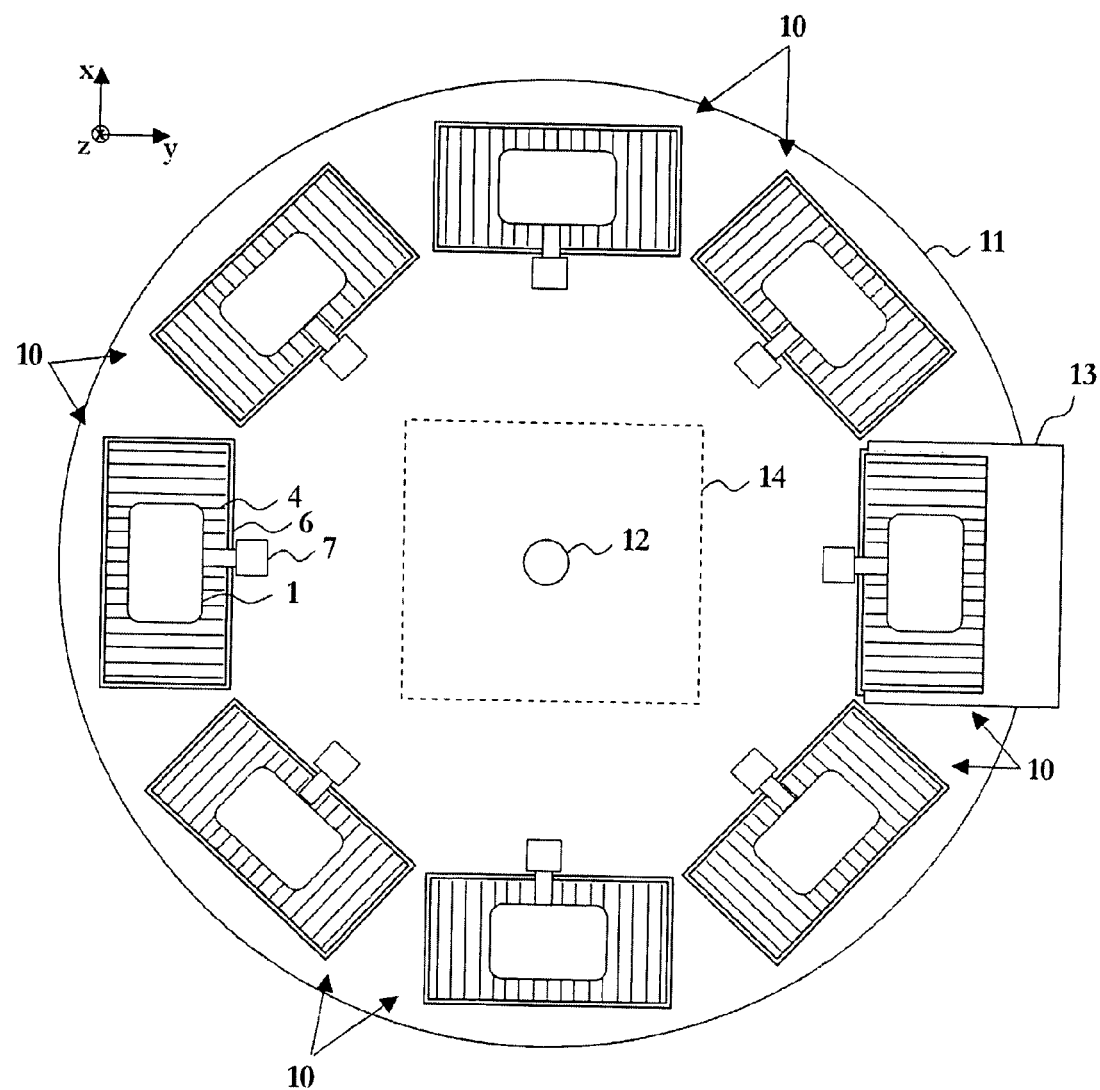
FIG. 3–4 illustrate each schematically, in a top view, an arrangement for obtaining tomosynthesis or other imaging data at high repetition rate for x-ray examination of an object according to a preferred embodiment of the present invention, the arrangement comprising a plurality of the apparatus of FIG. 1.

An arrangement for obtaining imaging data at high repetition rates for x-ray examination of an object according to a preferred embodiment of the present invention is schematically illustrated in FIG. 3 in top view. The arrangement comprises a plurality of the apparatus 10 of FIG. 1 arranged on a support structure 11 having an axis 12 of rotation. The apparatuses 10 are arranged on the support structure 11, which preferably consists of an essentially circular disk or plate, at essentially similar distances from the axis 12 of rotation, and preferably equiangularly around the axis 12 of rotation, i.e. adjacent ones of the apparatuses 10 are arranged with an essentially constant distance between them. The apparatuses 10 are standing on the support structure 11 so that the axis of symmetry 3 of the radiation 2, which is parallel with the z axis, is parallel with the normal of the support structure 11, which extends in the xy plane. The X-ray source 1, the collimator 4, the radiation detector 6, and the rigidly connecting structure 7 are clearly visible in FIG. 3.

Further, an object table 13 on which the object to be examined is provided. The object table 13 is initially arranged in the radiation path between the collimator 4 and the radiation detector 6 of one of the scanning-based apparatuses. Note that the object table is not supported by the support structure 11, but by another support structure (not illustrated).

A device 14 is provided for rotating the support structure 11 around the axis 12 of rotation relative the object table 13 so that the object table 13 will successively be arranged in the radiation path between the divergent radiation source and the radiation detector of each of the scanning-based apparatuses 10 of the arrangement. During the rotation each of the line detectors 6a of each of the scanning-based apparatuses 10 is adapted to record a plurality of line images of radiation as transmitted through the object in a respective one of different angles.

Note that the detector apparatuses 10 are preferably active in consecutive order. The X-ray radiation source 1 has thus only to be switched on during the time it is scanned across the object table 13 and thus has to produce radiation for the measurement.

Preferably, the device provided for rotating is adapted to rotate the support structure 11 relative the object table 13 at least an angle, e.g. one full revolution, which is sufficient for scanning each of the line detectors 6a of each of the scanning-based apparatuses 10 across the entire object to obtain, for each of the line detectors 6a of each of the scanning-based apparatuses 10, a two-dimensional image of radiation.

By means of the arrangement several sets of two-dimensional images for tomosynthesis reconstruction or any other kind of image reconstruction can be recorded, one after the other, without having to retard, stop and accelerate the detectors. The detectors are preferably simply rotated at a constant rotational speed.

Note that a difference in the scanning movement for each detector apparatus 10 is obtained relative the scanning disclosed in the U.S. patent application Ser. No. 10/657,241. In this application a linear scanning in the x direction is described, whereas in the present invention the scanning direction is along the periphery of a circle arranged in the xy plane. However, the larger the radius of the circle is, the more similar to a linear movement is obtained.

The distance between the detector apparatuses 10 and the axis 12 of rotation is preferably between about 0.5 m and about 4 m, more preferably between about 0.5 m and about 2 m, and most preferably about 1 m.

The more detector apparatuses that are arranged on the support structure 11, the higher repetition rate in the time-resolved recording is obtained for a given rotational speed of the support structure 11.

The number of the scanning-based apparatuses 10 is preferably between 2 and 20, more preferably between 2 and 10, and most preferably between 4 and 8. A typical figure is 5.

The device 14 provided for rotating is adapted to rotate said support structure 11 relative the object table 13 at a rotational speed of preferably between about 0.2 revolutions per second and about 10 revolutions per second, more preferably between about 0.5 revolutions per second and about 5 revolutions per second, and most preferably between about 0.5 revolutions per second and about 2 revolutions per second. A typical figure would be one full revolution per second.

This gives a repetition rate of between about 0.4 images/second and about 200 images/second for tomosynthesis. The typical figures given above correspond to a repetition rate of about 5 images per second. Each image is recorded at a number of angles, which correspond to the number of line detectors 6a in the stack of line detectors of each of the scanning-based apparatuses.

The different angles $\alpha_1, \alpha_n, \ldots, \alpha_N$ are distributed over an angular range $\alpha_N - \alpha_1$ of preferably at least 5°, more preferably at least 20°, and most preferably at least 45° depending on the application or kind of examination in order to obtain high-quality tomosynthesis data for examination of the object. A typical value is 90°. If other kind of measurements is to be performed, the angular range $\alpha_N-\alpha_1$ may naturally be much smaller. In some instances, the angular range $\alpha_N-\alpha_1$ might have to be minimized.

The length in the radial direction of each of the line detectors 6a in the stack of line detectors of each of the scanning-based apparatuses 10 is preferably between about 0.05 m and 2 m, more preferably between about 0.1 m and 1 m, and most preferably between about 0.2 m and 0.5 m. Similarly, the stack of line detectors of each of the scanning-based apparatuses 10 is preferably in the tangential direction between about 0.2 m and 2 m, more preferably between about 0.4 m and 1.5 m, and most preferably between about 0.75 m and 1.25 m. The sizes of the detector apparatuses 10 depend on the particular application the arrangement is to be used for.

The number of line detectors 6a in the stack of line detectors of each of the scanning-based apparatuses 10 is at least 2, preferably at least 5, more preferably at least 10, and most preferably between about 20 and about 100, depending on the number of images recorded at different angles, which is required during the examination. It can be as high as several hundred line detectors 6a.

The scanning step, in FIGS. 2a–c denoted by s1, sets a spatial resolution of the two-dimensional images formed from the one-dimensional recordings in the direction of the scanning. Typically, the scanning step s1 can be about 10–500 microns, and the individual detecting elements of each of the line detectors can be of similar size.

Figure 4:
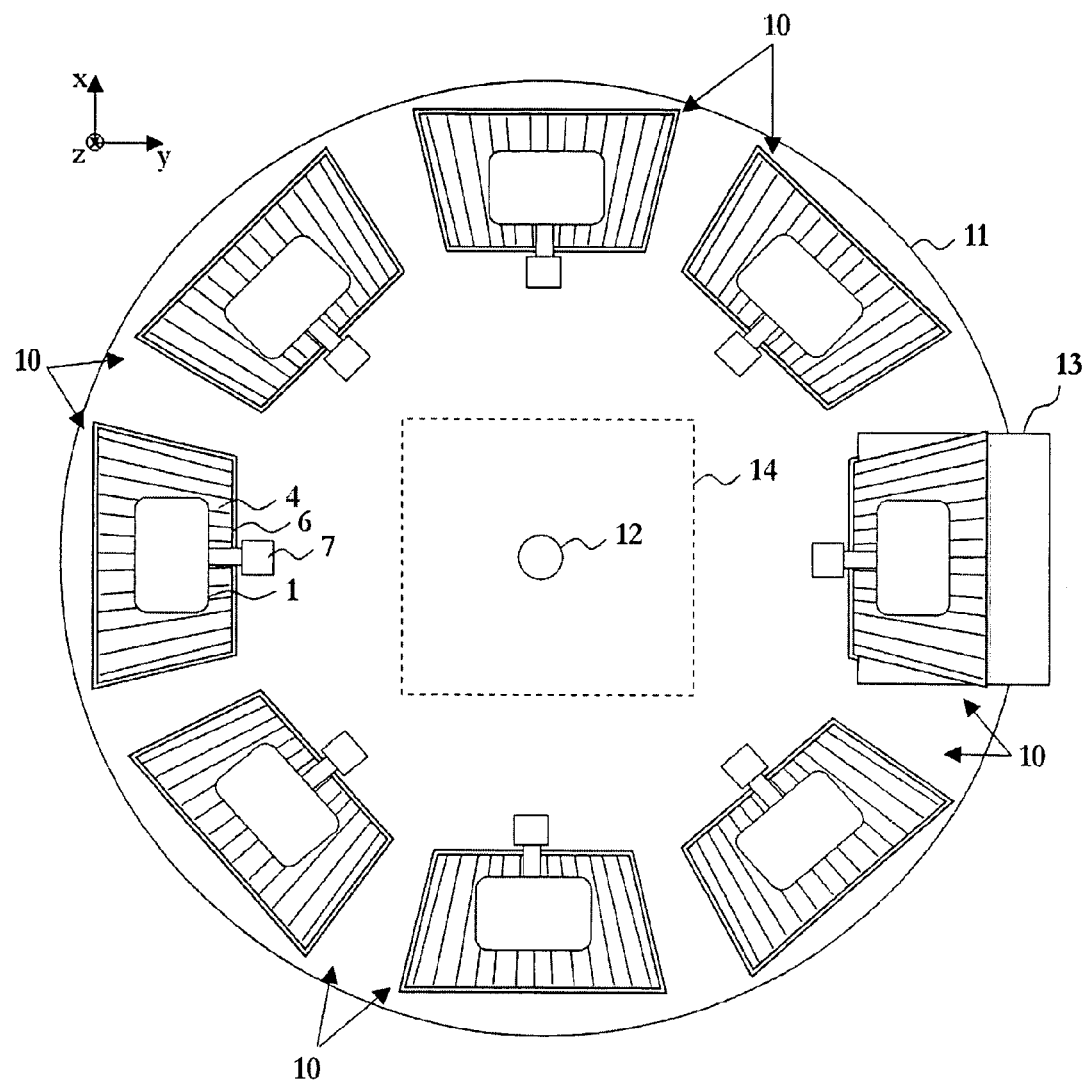

An arrangement for obtaining tomosynthesis or other imaging data at high repetition rates for x-ray examination of an object according to an alternative preferred embodiment of the present invention is schematically illustrated in FIG. 4 in top view. This embodiment is identical with the embodiment of FIG. 3 except for that the line detectors 6a of each detector apparatus 10 are arranged 11 radially with respect to the axis 12 of rotation instead of being arranged parallel with each other within each detector apparatus 10. Any reconstruction model has naturally to be modified to deal with the non-parallel arrangement of the line detectors 6a.

For general two-dimensional transmission image recordings the scanning-based arrangement may typically have the following dimensions. The support structure may have a radius of 1 m, the line detectors may be 20 cm long and be arranged radially at the periphery of the support structure 1 cm apart from each other. Six scanning-based apparatuses are provided, each of which includes about 100 line detectors pointing towards a respective radiation source arranged about 1.5 m above the line detectors. The rotational speed during scanning may be e.g. 0.01–1 full revolution per second. It can also be more, or less, limited mainly by the mechanical forces on the equipment and the X-ray flux from the X-ray tube (as well as the transmission of the object) to get sufficient X-rays detected in each image pixel to produce an image of high quality.

Preferably, the rotational speed is selected such that at least one two-dimensional transmission image per second can be formed.

Three different variants can be distinguished:

In the first variant, the two-dimensional transmission images can be reconstructed by an image processing device by building up or forming each of the two-dimensional transmission images from line images of radiation from one of the line detectors in one of the radiation detectors, i.e. each line detector is responsible for recording all line images, by which a two-dimensional transmission image is formed. The number of two-dimensional transmission images reconstructed is equal to the product of the number of said plurality of scanning-based apparatuses and the number of line detectors in each of said radiation detectors for each full revolution that said support structure is rotated.

For angiocardiography the heart of a patient is examined time-dependently. Given a heart size of e.g. 16 cm, a rotational speed of 0.01 full revolutions per second and the detector characteristics above, the time for scanning a line detector across the heart is approximately 2.5 seconds. Given a scanning step of e.g. 0.1 mm gives an exposure time of 1.5 ms for each single instantaneously recorded line image. 6 two-dimensional transmission images per second are taken even though they are taken (exposed) during overlapping time periods.

In the second variant, the two-dimensional transmission images are reconstructed by an image processing device by building up each of the two-dimensional transmission images from line images of radiation from the line detectors in one of the radiation detectors as recorded during scanning a distance corresponding to the distance between adjacent ones of the line detectors in the radiation detector, i.e. all line detectors in a radiation detector that covers the object are together responsible for recording the line images, by which a two-dimensional transmission image is formed.

Given the figures above about 16 line detectors cover the heart, and thus each two-dimensional transmission image is formed from line images as taken by 16 line detectors during scanning. With a rotational speed of 0.16 full revolutions per second, the exposure time for each image will then be approximately 10 ms and 100 two-dimensional transmission images per second will be taken, one after the other.

In the third variant, the two-dimensional transmission images are reconstructed by an image processing device by building up each line of each of the two-dimensional transmission images from one line image of radiation from each of the line detectors of one of the radiation detectors, i.e. all line detectors in a radiation detector are together responsible for recording the line images, by which a two-dimensional transmission image is formed. Each line in the two-dimensional transmission image is formed from line images as taken by all line detectors in the radiation detector at a given position. The number of two-dimensional transmission images reconstructed is equal to the number of scanning-based apparatuses for each full revolution that said support structure is rotated.

Given the figures above and a rotational speed of 1 full revolution per second, the exposure time for a two-dimensional transmission image is about 160 ms, and 6 images per second are taken.

When imaging, at a given repetition rate, a periodic event, i.e. an event that recurs at intervals, such as e.g. heart beats, the time resolution of the series of two-dimensional images can be made shorter than the sample rate of the imaging by combining imaging data from several heart beats. This method is especially efficient if the frequency of the heart beat and the frequency of the image sampling are not integer multiples of one another, but a phase shift is obtained in the series of images between each heart beat.

A preferred line detector for use in the present invention is a gaseous-based parallel plate detector, preferably provided with an electron avalanche amplifier. Such a gaseous-based parallel plate detector is an ionization detector, wherein electrons freed as a result of ionization by ionizing radiation are accelerated in a direction essentially perpendicular to the direction of the radiation.

For further details regarding such kind of gaseous-based line detectors for use in the present invention, reference is made to the following U.S. Patents by Tom Francke et al. and assigned to XCounter AB of Sweden, which patents are hereby incorporated by reference: U.S. Pat. Nos. 6,546,070; 6,522,722; 6,518,578; 6,118,125; 6,373,065; 6,337,482; 6,385,282; 6,414,317; 6,476,397; and 6,477,223. It shall particularly be pointed out that such kind of detector is very efficient in preventing Compton scattered radiation from being detected. This property is of outermost importance to obtain high-quality tomosynthesis data.

Further, such kind of detector has been found to be extremely sensitive and can in principle be adapted for single-photon detection, which is important when studying very fast processes.

The distance between the parallel plates, i.e. electrodes, of the line detector may be below about 2 mm, preferably below about 1 mm, more preferably below about 0.5 mm, and most preferably between about 0.1 mm and 0.5 mm. XCounter AB has recently begun to verify the Compton scattering rejection characteristics of the line detector experimentally and good contrast has been observed using a wide X-ray spectrum of high energy X-rays, at which conditions a conventional detector system would not be capable to see any structure at all. It is believed that the above-depicted gaseous-based line detector discriminates more than 99% of the scattered photons; and by proper design it is assumed that about 99.9% or more of the scattered photons can be prevented from being detected.

It shall, nevertheless, be realized that any other type of detector may be used in the present invention. Such line detectors include scintillator-based arrays, CCD arrays, TFT- and CMOS-based detectors, liquid detectors, and solid-state detectors such as one-dimensional PIN-diode arrays with edge-on, near edge-on or perpendicular incidence of X-rays, possibly with a collimator structure in front to partly reject scattered X-rays.

It shall further be noted that that the structure 7 for rigidly connecting the X-ray source 1, the collimator 4, and the radiation detector 6 may be exchanged for separate devices (not illustrated) for the X-ray source 1, the collimator 4 and the radiation detector 6, which may be controlled electronically to obtain synchronous linear movements of the separate devices to obtain the similar scanning movement.

It shall yet further be noted that instead of keeping the object still and rotating the support structure around the axis of rotation, the support structure may be kept still and the object may be rotated around the axis of rotation. This may particularly be advantageous in case the object to be examined is not a patient that is awake.

In order to be capable of recording images of the object at still further angles, the object may be rotated or otherwise moved on the object table, or the support structure, which carries the scanning-based apparatuses 10, may be tilted, after which scanning is performed by means of rotating the support structure around a new axis of rotation, which is orthogonal to the plane of the support structure.

It shall be noted that for all three two-dimensional imaging variants described above, each image is taken at a slightly different angle through the object than the previous due to the angle of the detector in correspondence to the vertical axis. This sequence of imaging angles is repeated for each radiation detector 6 used for the image acquisition. This is advantageous in e.g. angiography where it is beneficial to see the heart from many different angles. With this method the heart can be imaged from many angles for a single contrast agent injection. It is also beneficial in mammography, or any other tumor search, where the tumor can be hidden behind a dense object in one view, but visible at a different angle.

It shall still further be noted that the radiation detector 6 of the apparatus of FIG. 1 may be modified such that the line detectors, instead of being arranged in a linear stack, are arranged at the periphery of a circle, the center of which coinciding with the position of radiation source 1.

Advantages of the present invention include:

A large number of consecutive images can be recorded during a short period of time. The number is set by the number of scanning-based detector apparatuses used, the number of line detectors in each scanning-based detector apparatus, the rotational speed of the scanning movement, and the choice of reconstruction model.

The forces on the detector apparatuses, i.e. the radiation sources and the radiation detectors are small and constant in time. No mechanical vibrations will occur.

Only one or two X-ray tubes have to be switched on at a time, which means that each X-ray source can be cooled except when it is required for the measurement, i.e. from when it begins to overlap with the object table 13 until its radiation beam has scanned across the object completely. As a consequence, a large number of consecutive images per second can be recorded without overheating the X-ray tubes. Typically, an X-ray source is switched on during $\frac{1}{6}$ to $\frac{1}{3}$ of the scanning time, which implies that the power can be increased 3–6 times when the radiation source is switched on as compared with a maximum continuous power. A control device may be provided for controlling the switching of the X-ray tubes or other radiation sources used.

Cheaper X-ray tubes can be used since it does not need to have a large heat capacity.

There are no limitations whatsoever regarding the width and length of the scanning-based detector apparatuses in the arrangement. The larger widths the scanning-based detector apparatuses have, the larger tomosynthesis angle is obtained. The length of each line detector may be limited. If a longer line detector is needed, several line detectors may be arranged side by side in order to together simulate one long line detector. Such arrangement is disclosed in the published U.S. Patent Application No. 20030155518 by Tom Francke, the contents of which being hereby incorporated by reference.

By arranging the line detectors far from the axis of rotation, the pixels will be closer to quadratic in shape, and the reconstruction will be faster and easier. The scanning will be more similar a linear scanning. Further, the line detectors may be arranged closer to each other (packed more densely) since the distance between two adjacent line detectors is very similar at its far ends (the radially inner end and the radially outer end) due to the large radius of the support structure and the positions of the line detectors.

The rays of ionizing radiation will almost impinge onto the line detectors at normal incidence since the radiation sources are located right above the line detectors at the periphery of the support structure.

The dose to the patient is lower compared to CT.

The exposure time is short which means that any blurredness due to movement of or by the object is minimized.

By using the gaseous-based parallel plate detector, preferably provided with an electron avalanche amplifier described above a rather cheap arrangement can be provided, with radiation detectors which are direction sensitive, i.e. they have extremely low noise from scattered photons, and which have no electronic noise, i.e. they provide for photon counting with excellent signal-to-noise ration for individual photons.

What is claimed is:

1. A scanning-based arrangement for obtaining imaging data of an object at high repetition rate comprising:
   a support structure having an axis of rotation;
   a plurality of scanning-based apparatuses fixedly arranged on said support structure at an essentially similar distance from said axis of rotation, each of said plurality of scanning-based apparatuses including:
      a radiation source emitting radiation centered around an axis of symmetry; and
      a radiation detector comprising a stack of line detectors for creating the imaging data, each line detector being directed towards the radiation source to allow a ray bundle of said radiation to enter the line detector;
   an object table on which said object is arranged, said object table being arranged in the radiation path between the radiation source and the radiation detector of one of said plurality of scanning-based apparatuses; and
   a device provided for rotating said support structure around said axis of rotation relative said object table so that said object table will successively be arranged in the radiation path between the divergent radiation source and the radiation detector of each of said plurality of scanning-based apparatuses, during which rotation each of the line detectors of each of said radiation detectors is adapted to record, at high repetition rate, a plurality of line images of radiation as transmitted through said object, wherein
   said axis of rotation is substantially parallel with each of said axes of symmetry.

2. The arrangement of claim 1 wherein said imaging data at high repetition rate is tomosynthesis data; each of said radiation sources is divergent; and the line detectors in each of said radiation detectors are directed towards a respective one of said divergent radiation sources to allow ray bundles of the radiation from the divergent radiation source that propagate in different angles to each enter a respective one of the line detectors, wherein the line detectors in each of said radiation detectors are each adapted to record a plurality of line images of radiation as transmitted through said object in a respective one of said plurality of different angles to provide said tomosynthesis data.

3. The arrangement of claim 2 wherein said plurality of different angles is distributed over an angular range of at least 5°.

4. The arrangement of claim 2 wherein said plurality of different angles is distributed over an angular range of at least 20°.

5. The arrangement of claim 2 wherein said plurality of different angles is distributed over an angular range of at least 45°.

6. The arrangement of claim 2 comprising an image processing device adapted for reconstructing two- or three-dimensional images of said object from said tomosynthesis data by means of performing a tomosynthesis reconstruction calculation.

7. The arrangement of claim 1 wherein said imaging data at high repetition rate is data for reconstructing two-dimensional transmission images.

8. The arrangement of claim 7 comprising an image processing device adapted for reconstructing said two-dimensional transmission images, the number of which being equal to the number of said plurality of scanning-based apparatuses for each full revolution that said rotating device rotates said support structure.

9. The arrangement of claim 8 wherein said image processing device is adapted for reconstructing said two-dimensional transmission images so that each line of each of said two-dimensional transmission images is formed from one line image of radiation from each of the line detectors in one of said radiation detectors.

10. The arrangement of claim 7 comprising an image processing device adapted for reconstructing said two-dimensional transmission images, the number of which being equal to the product of the number of said plurality of scanning-based apparatuses and the number of line detectors in each of said radiation detectors for each full revolution that said rotating device rotates said support structure.

11. The arrangement of claim 10 wherein said image processing device is adapted for reconstructing said two-dimensional transmission images so that each line of each of said two-dimensional transmission images is formed from one line image of radiation from one of the line detectors in one of said radiation detectors.

12. The arrangement of claim 11 wherein said image processing device is adapted for reconstructing said two-dimensional transmission images so that each of said two-dimensional transmission images is formed from line images of radiation from one of the line detectors in one of said radiation detectors.

13. The arrangement of claim 11 wherein said image processing device is adapted for reconstructing said two-dimensional transmission images so that each of said two-dimensional transmission images is formed from line images of radiation from the line detectors in one of said radiation detectors as recorded during scanning a distance corresponding to the distance between adjacent ones of the line detectors in said one of said radiation detectors.

14. The arrangement of claim 7 comprising a fluoroscopy apparatus for visualizing, at high repetition rate, radiation as transmitted through said object.

15. The arrangement of claim 7 wherein said data for reconstructing two-dimensional transmission images is angiography data.

16. The arrangement of claim 1 wherein the number of said plurality of scanning-based apparatuses is between 2 and 20.

17. The arrangement of claim 1 wherein the number of said plurality of scanning-based apparatuses is between 2 and 10.

18. The arrangement of claim 1 wherein the number of said plurality of scanning-based apparatuses is between 4 and 8.

19. The arrangement of claim 1 wherein said plurality of scanning-based apparatuses is arranged equiangularly around said axis of rotation.

20. The arrangement of claim 1 wherein said essentially similar distance is between about 0.5 m and about 4 m.

21. The arrangement of claim 1 wherein said essentially similar distance is between about 0.5 m and about 2 m.

22. The arrangement of claim 1 wherein said essentially similar distance is about 1 m.

23. The arrangement of claim 1 wherein said device provided for rotating is adapted to rotate said support structure relative said object table at a rotational speed of between about 0.01 revolutions per second and about 10 revolutions per second.

24. The arrangement of claim 1 wherein said device provided for rotating is adapted to rotate said support structure relative said object table at a rotational speed of between about 0.5 revolutions per second and about 5 revolutions per second.

25. The arrangement of claim 1 wherein said device provided for rotating is adapted to rotate said support structure relative said object table at a rotational speed of between about 0.5 revolutions per second and about 2 revolutions per second.

26. The arrangement of claim 1 wherein the length of each of the line detectors in the stack of line detectors in each of said radiation detectors is between about 0.05 m and 2 m.

27. The arrangement of claim 1 wherein the length of each of the line detectors in the stack of line detectors in each of said radiation detectors is between about 0.1 m and 1 m.

28. The arrangement of claim 1 wherein the length of each of the line detectors in the stack of line detectors in each of said radiation detectors is between about 0.2 m and 0.5 m.

29. The arrangement of claim 1 wherein a width of the stack of line detectors in each of said radiation detectors is between about 0.2 m and 2 m.

30. The arrangement of claim 1 wherein a width of the stack of line detectors in each of said radiation detectors is between about 0.4 m and 1.5 m.

31. The arrangement of claim 1 wherein a width of the stack of line detectors in each of said radiation detectors is between about 0.75 m and 1.25 m.

32. The arrangement of claim 1 wherein the number of line detectors in the stack of line detectors in each of said radiation detectors is at least 2.

33. The arrangement of claim 1 wherein the number of line detectors in the stack of line detectors in each of said radiation detectors is at least 5.

34. The arrangement of claim 1 wherein the number of line detectors in the stack of line detectors in each of said radiation detectors is between about 20 and about 100.

35. The arrangement of claim 1 wherein the line detectors in each of said radiation detectors are arranged parallel with each other.

36. The arrangement of claim 1 wherein each of the line detectors in the stack of line detectors in each of said radiation detectors is arranged radially with respect to said axis of rotation.

37. The arrangement of claim 1 wherein the divergent radiation source of each of said scanning-based apparatuses is an X-ray source; and the radiation detector of each of said scanning-based apparatuses is a gaseous-based ionization detector, wherein electrons freed as a result of ionization by a respective ray bundle are accelerated in a direction essentially perpendicular to the direction of that ray bundle.

38. The arrangement of claim 33 wherein said gaseous-based ionization detector is an electron avalanche detector.

39. The arrangement of claim 1 wherein the radiation detector of each of said scanning-based apparatuses is any of a diode array, a scintillator-based array, a CCD array, a TFT- or CMOS-based detector, or a liquid detector.

40. The arrangement of claim 1 wherein each of said scanning-based apparatuses comprises a collimator arranged in the radiation path immediately downstream of the radiation source of that scanning-based apparatus, said collimator preventing radiation, which is not directed towards the line detectors of that scanning-based apparatus, from impinging on said object, thereby reducing the radiation dose to said object.

41. The arrangement of claim 1 comprising a control device for switching on and off said radiation sources, said control device being provided to switch on and off said radiation sources in a consecutive order so that each of said radiation sources can be switched off and cooled while the object is not present in the radiation path of the scanning-based apparatus, in which the radiation source is comprised.

42. The arrangement of claim 1 wherein each of the line detectors in the radiation detectors is arranged at a distance from the axis of rotation which is longer than the length of each of the line detectors in the radiation detectors.

43. A scanning-based method for obtaining imaging data of an object at high repetition rate using a scanning-based arrangement comprising a support structure having an axis of rotation; and a plurality of scanning-based apparatuses fixedly arranged on said support structure at an essentially similar distance from said axis of rotation, each of said plurality of scanning-based apparatuses including a radiation source emitting radiation centered around an axis of symmetry, and a radiation detector comprising a stack of line detectors for creating the imaging data, each line detector being directed towards the radiation source to allow a ray bundle of said radiation to enter the line detector, said method comprising the steps of:
arranging said object in the radiation path between the radiation source and the radiation detector of one of said plurality of scanning-based apparatuses; and
rotating said support structure around said axis of rotation relative said object so that said object will successively be arranged in the radiation path between the divergent radiation source and the radiation detector of each of said plurality of scanning-based apparatuses, during which rotation, by means of each of said line detectors of each of said radiation detectors, a plurality of line images of radiation as transmitted through said object is recorded at high repetition rate, wherein
said axis of rotation is substantially parallel with each of said axes of symmetry.

44. The method of claim 43 wherein said imaging data at high repetition is provided as tomosynthesis data; the radiation from each of said radiation sources is emitted in a divergent radiation beam; and the line detectors in each of said radiation detectors are directed towards a respective one of said divergent radiation sources to allow ray bundles of the radiation from the radiation source that propagate in different angles to each enter a respective one of the line detectors, wherein a plurality of line images of radiation as transmitted through said object in a respective one of said plurality of different angles are recorded by the line detectors in each of said radiation detectors to provide said tomosynthesis data.

45. The method of claim 44 wherein two- or three-dimensional images of said object are reconstructed from said tomosynthesis data by means of performing a tomosynthesis reconstruction calculation.

46. The method of claim 43 wherein said imaging data at high repetition rate is provided as data for reconstructing two-dimensional transmission images.

47. The method of claim 46 wherein said two-dimensional transmission images, the number of which being equal to the number of said plurality of scanning-based apparatuses for each full revolution that said support structure is rotated, are reconstructed by building up each line of each of said two-dimensional transmission images from one line image of radiation from each of the line detectors of one of said radiation detectors.

48. The method of claim 46 wherein said two-dimensional transmission images, the number of which being equal to the product of the number of said plurality of scanning-based apparatuses and the number of line detectors in each of said radiation detectors for each full revolution that said support structure is rotated, are reconstructed by building up each of said two-dimensional transmission images from line images of radiation from one of the line detectors in one of said radiation detectors.

49. The method of claim 46 wherein said two-dimensional transmission images, the number of which being equal to the product of the number of said plurality of scanning-based apparatuses and the number of line detectors in each of said radiation detectors for each full revolution that said support structure is rotated, are reconstructed by building up each of said two-dimensional transmission images from line images of radiation from the line detectors in one of said radiation detectors as recorded during scanning a distance corresponding to the distance between adjacent ones of the line detectors in said one of said radiation detectors.

50. The method of claim 43 wherein radiation as transmitted through said object is visualized, at high repetition rate, by a fluoroscopy method.

51. The method of claim 43 wherein said imaging data of said object is angiography imaging data.

52. The method of claim 43 wherein said radiation sources are switched on and off in a consecutive order so that each of said radiation sources can be switched off and cooled while the object is not present in the radiation path of the scanning-based apparatus, in which the radiation source is comprised.

53. The method of claim 43 wherein said object performs a periodic event; imaging data from several cycles of said periodic event is recorded; and imaging data from said several cycles are combined to increase the temporal resolution of the imaging data of the periodic event.

54. The method of claim 53 wherein said periodic event is heart beats by the heart of a patient.

55. The method of claim 53 wherein said high repetition rate is selected relative the frequency of the periodic event so that said high repetition rate and said frequency of the periodic event are not integer multiples of one another.

56. A scanning-based arrangement for obtaining tomosynthesis data of an object comprising:
  a support structure having an axis of rotation;
  a plurality of scanning-based apparatuses fixedly arranged on said support structure, each of said plurality of scanning-based apparatuses including:
    a divergent radiation source emitting radiation centered around an axis of symmetry; and
    a radiation detector comprising an array of one-dimensional detectors for creating the tomosynthesis data, each one-dimensional detector being directed towards the divergent radiation source to allow a ray bundle of said radiation that propagates in a respective one of a plurality of different angles to enter the one-dimensional detector;
  an object support for supporting said object, said object support being arranged in the radiation path between the divergent radiation source and the radiation detector of one of said plurality of scanning-based apparatuses; and
  a device provided for rotating said support structure around said axis of rotation relative said object support so that said object support will successively be arranged in the radiation path between the divergent radiation source and the radiation detector of each of said plurality of scanning-based apparatuses, during which rotation each of the one-dimensional detectors of each of said plurality of scanning-based apparatuses is adapted to record a plurality of one-dimensional images of radiation as transmitted through said object in a respective one of said plurality of different angles, wherein
  said axis of rotation is substantially parallel with each of said axes of symmetry.

57. A scanning-based arrangement for obtaining two-dimensional transmission images of an object comprising:
  a support structure having an axis of rotation;
  a plurality of scanning-based apparatuses fixedly arranged on said support structure, each of said plurality of scanning-based apparatuses including:
    a radiation source emitting radiation centered around an axis of symmetry; and
    a radiation detector comprising an array of one-dimensional detectors for creating the two-dimensional transmission image data, each one-dimensional detector being directed towards the radiation source to allow a ray bundle of said radiation to enter the one-dimensional detector;
  an object support for supporting said object, said object support being arranged in the radiation path between the radiation source and the radiation detector of one of said plurality of scanning-based apparatuses; and
  a rotating device provided for rotating said support structure around said axis of rotation relative said object support so that said object support will successively be arranged in the radiation path between the radiation source and the radiation detector of each of said plurality of scanning-based apparatuses, during which rotation each of the one-dimensional detectors of each of said plurality of scanning-based apparatuses is adapted to record, at high repetition rate, a plurality of one-dimensional images of radiation as transmitted through said object to thereby be capable of reconstructing two-dimensional transmission images at high repetition rate from said plurality of one-dimensional images of radiation recorded at high repetition rate, wherein
  said axis of rotation is substantially parallel with each of said axes of symmetry.

* * * * *